United States Patent [19]

Takata et al.

[11] Patent Number: 4,806,250

[45] Date of Patent: Feb. 21, 1989

[54] LIQUID CHROMATOGRAPHY AND APPARATUS USING THE SAME

[75] Inventors: Yoshinori Takata, Chiba; Mitsuo Ito, Ibaraki; Junkichi Miura, Hitachi, all of Japan

[73] Assignee: Hitachi, Ltd., Tokyo, Japan

[21] Appl. No.: 161,180

[22] Filed: Feb. 26, 1988

Related U.S. Application Data

[63] Continuation of Ser. No. 940,487, Dec. 10, 1986, abandoned.

[30] Foreign Application Priority Data

Dec. 12, 1985 [JP] Japan .................... 60-280049

[51] Int. Cl.⁴ .............................. B01D 15/08
[52] U.S. Cl. .................... 210/659; 210/198.2
[58] Field of Search ........... 210/635, 656, 659, 198.2; 422/70

[56] References Cited

U.S. PATENT DOCUMENTS

| | | | |
|---|---|---|---|
| 3,467,595 | 9/1969 | Sten | 210/198.2 |
| 3,686,117 | 8/1972 | Lauer | 210/659 |
| 3,925,207 | 12/1975 | Scriba | 210/198.2 |
| 4,042,499 | 8/1977 | Ramstad | 210/659 |
| 4,070,284 | 1/1978 | Fujita | 210/659 |
| 4,154,583 | 5/1979 | Favre | 210/198.2 |
| 4,364,263 | 12/1982 | Sankoorikal | 210/198.2 |
| 4,478,713 | 10/1984 | Girot | 210/198.2 |
| 4,478,720 | 10/1984 | Perrut | 210/659 |
| 4,500,432 | 2/1985 | Poole | 210/659 |
| 4,604,198 | 8/1986 | Dailey | 210/198.2 |

FOREIGN PATENT DOCUMENTS

60-29664 2/1985 Japan ................... 210/659

OTHER PUBLICATIONS

Kirkland, Introduction to Modern Liquid Chromatography, Wiley & Sons, Inc., New York, 1979, pp. 646-647.
Hawley, The Condensed Chemical Dictionary, Van Nostrand Reinhold Co., New York, 1971, p. 402.

Primary Examiner—Ernest G. Therkorn
Attorney, Agent, or Firm—Antonelli, Terry & Wands

[57] ABSTRACT

Desired components can be simply and economically separated and recovered from a sample solution having a complicated composition through a liquid chromatography by passing the sample solution through a separation column, thereby separating components contained therein in the separation column, then selectively passing the eluate from the separation column through a trapping column according to a desired component, thereby trapping the desired component in the trapping column, while discarding or recycling the effluent eluate from the trapping column, and then passing another eluting solution composed of a volatile substance when dried under reduced pressure through the trapping column, thereby recovering eluate containing the desired component from the trapping column.

6 Claims, 4 Drawing Sheets

RETENTION TIME (min.)

RETENTION TIME (min.)

LIQUID CHROMATOGRAPHY AND APPARATUS USING THE SAME

This application is a continuation of application Ser. No. 940,487 filed Dec. 10, 1986, now abandoned.

BACKGROUND OF THE INVENTION

This invention relates to a liquid chromatography and an apparatus using the same.

In chromatographic separation of samples having complicated compositions such as proteins, peptides, and DNA into the respective components, aqueous solutions of salts which leave a large amount of involatile powder as such when subjected to drying under reduced pressure, for example, a phosphate buffer, etc., are used as eluting solutions. Thus, the ultimate products are obtained in the form of mixtures containing a trace amount of desired components in a large amount of phosphates, necessitating further separating operations such as solvent extraction, centrifuge, etc. to isolate the desired component, and thus complicating the separation procedure. Furthermore, if the amount of the fractionated solution is large, the yield will be lowered. It will take about one week to obtain 90% yield, whereas only about 50% yield is obtained a one-day operation.

Japanese Patent Application Kokai (Laid-open) No. 60-29664 discloses a liquid chromatographic art of saving the amount of an eluting solution, based on fractionated recovery, by detecting the rise points and the end points of the respective peaks of components in an eluate by means of a detector, discharging fractions of eluate corresponding to the peak regions by means of a three-way switch valve, and recovering for reuse those eluate fractions that have no adverse effect on the background. discloses Furthermore, U.S. Pat. No 4,070,284 discloses an art of accumulating and concentrating desired components contained in a large amount of a sample solution in a low concentration by means of a plurality of detachable concentration columns in advance and then passing the concentrated solutions through a liquid chromatographic separation column.

SUMMARY OF THE INVENTION

An object of the present invention is to provide a liquid chromatography with much simplified isolation of the desired component and an apparatus using the same.

In the conventional liquid chromatography, the separation column eluate is fractionated into the respective fraction collectors to recover the fractions of desired components eluted in a large amount of eluting solution, whereas in the present invention a trapping column is used in place of the fraction collectors, and the separation column eluate is selectively fractionated according to the components to pass the eluate fraction through the trapping column, thereby trapping only the desired component in the trapping column, while discarding the effluent eluate from the trapping column as such or recycling it. Then, the desired component trapped in the trapping column is eluted with a small amount of another eluting solution. Another eluting solution for use in the present invention is composed of a volatile component when dried under reduced pressure.

That is, according to a first aspect of the present invention, a liquid chromatography for isolating the desired component from a sample solution having a complicated composition is provided, which comprises passing the sample solution through a separation column, thereby separating components contained therein through the separation column, then selectively passing the eluate from the separation column through a trapping column according to a desired component, thereby trapping the desired component in the trapping column, while discarding or recycling the effluent eluate from the trapping column, and then passing another eluting solution composed of a volatile substance when dried under reduced pressure through the trapping column, thereby recovering elutate containing the desired component from the trapping column.

According to a second aspect of the present invention a liquid chromatographic apparatus is provided, which comprises a means of supplying an eluting solution, a means of supplying a sample solution, a separation column, a plurality of trapping columns through which an eluate from the separation column is selectively passed, a means of selectively supplying the eluate from the separation column to the respective trapping columns according to desired components contained in the eluate from the separation column, and a means of supplying another eluting solution to the respective trapping columns, thereby obtaining eluates containing the desired components respectively.

Furthermore, in the present invention, the eluate fraction from the separation column is subjected to detection of components in the eluate fraction by means of a detector, and selectively led to one of trapping columns according to the detected desired component. The detector and the introduction of the eluate fraction containing the detected desired component to the trapping column are interlocked with each other, and furthermore the introduction of the eluting solution to the trapping column and the recovery of the resulting eluate therefrom are also interlocked with each other. That is, structurally in the present invention, the means of supplying another eluting solution to the respective trapping columns, thereby obtaining eluates containing the desired components respectively, is connected to the means of selectively passing anothe eluting solution to the respective trapping columns through a switching means, and the switching means is interlocked with a detector. The trapping columns may be of a detachable type.

PREFERRED EMBODIMENTS OF THE INVENTION

Structural and operating principles of the present invention will be described below, referring to FIGS. 1 to 3.

Figure 1:
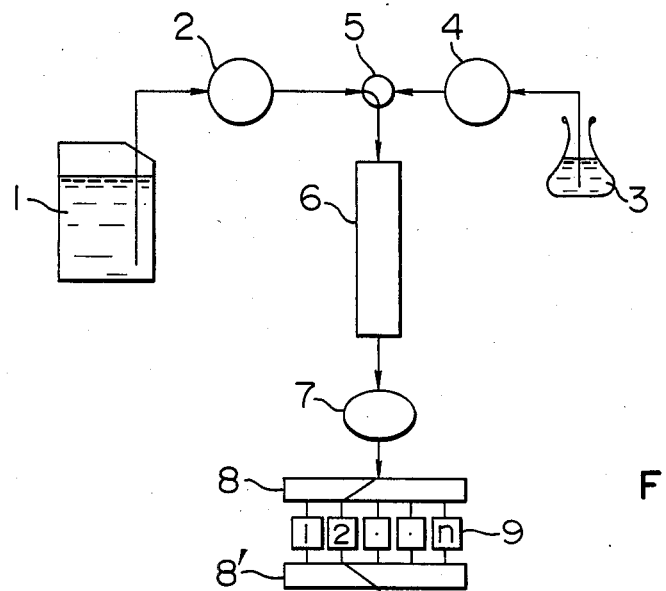
FIG. 1 and FIG. 2 are schematic arrangements showing the principle of the present liquid chromatography, respectively.
Figure 2:
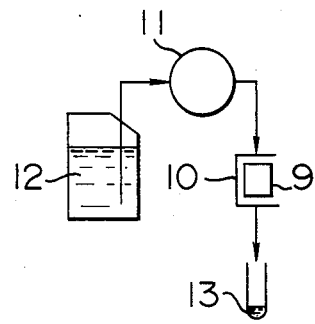

In FIGS. 1 and 2, arrangements of the present liquid chromatography are shown according to one embodiment, which is composed essentially of a pump 2 for supplying an eluting solution 1 to a separation column 6, a pump 4 for supplying a sample solution 3 to the separation column 6, a switch valve 5 for supplying the sample solution or the eluting solution to the separation column 6, the separation column 6, a detector 7, multiway, interlocked valves 8 and 8', and n trapping columns 9 provided between the multi-way, interlocked valves 8 and 8'.

In carrying out the present liquid chromatography, the sample solution 3 is supplied to the separation column 6 by the pump 4 through the switch valve 5. Then, the eluting solution 1 is supplied to the separation column 6 by the pump 2 through the switch valve 5 to develop and separate the components adsorbed in the separation column 6, and the resulting eluate from the separation column 6 is detected by a detector 7 to obtain a chromatogram of the components contained in the eluate. In accordance with the peaks of the desired components on the chromatogram, interlocked multiway valves 8 and 8' are switched to supply the eluate fractions with the respective desired components into the respective trapping columns 9 to trap the desired components therein, while discharging the effluent eluate fractions from the trapping column as such. The trapping columns 9 are of a detachable type, and the desired component-trapped columns 9 are transferable into a column holder 10, as shown in FIG. 2, and the trapped desired components are eluated by another eluting solution 12 supplied by a pump 11 and collected as desired component solutions 13, respectively.

Figure 3:
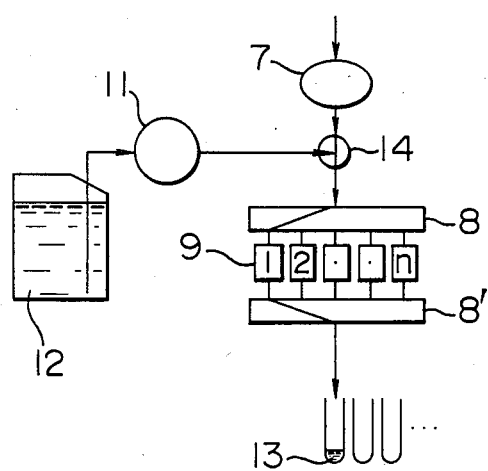
FIG. 3 shows another mode of the present liquid chromatography.

FIG. 3 shows par of another arrangement according to further embodiment of the present invention, where the omitted parts are identical with the corresponding parts shown in FIG. 1, and members identical with those sown in FIG. 1 are identified with the same reference reference numerals as in FIG. 1. According to the embodiment of FIG. 3, a switch valve 14 is provided in the flow line between the detector 7 and the interlocked multi-way valve 8 to supply another eluting solution 12 to the respective specific trapping column 9 by a pump 11. Thus, the eluting solution 12 can be supplied to the trapping column 9 without any trouble of removing the trapping columns 9 from between the interlocked multi-way valves 8 and 8' and transferring them into the column holder 10, as shown in FIG. 2.

Specific modes of carrying out the present invention will be described in detail below, referring to FIGS. 4 to 7.

Figure 4:
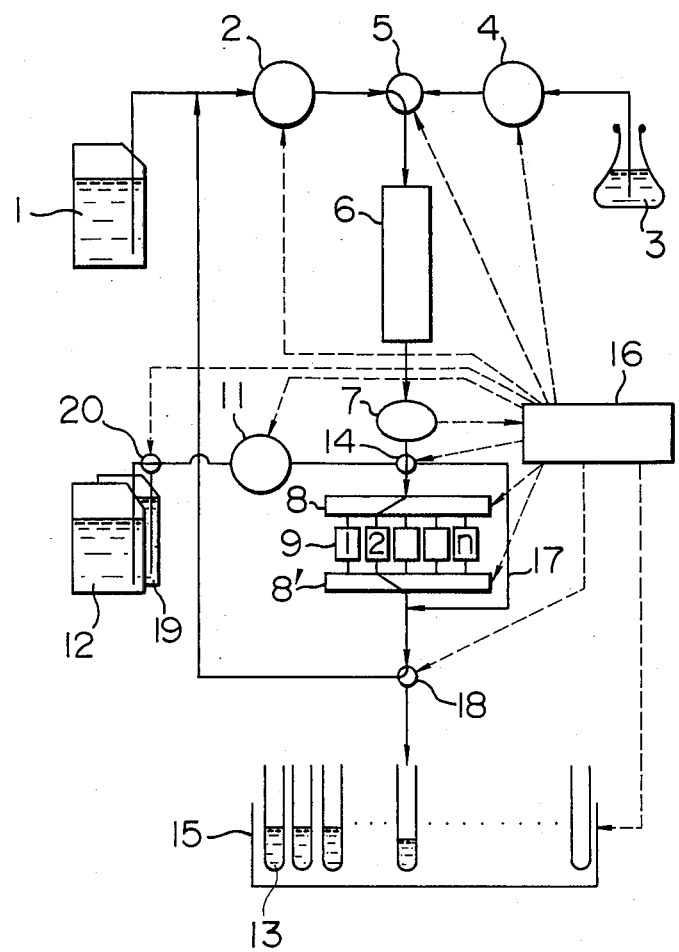
FIG. 4 shows one embodiment of specific mode of carrying out the present liquid chromatography.

Fractionating and recovery system of the present liquid chromatography shown in FIG. 4 comprises a separating, fractionating and trapping section comprising a pump 2 for supplying an eluting solution 1 to a separation column 6, a pump 4 for supplying a sample solution 3 to the separation column 6, a switch valve 5 for supplying the eluting solution 1 to the separation column 6 after the supply of the sample solution 3 thereto, the separation column 6, a detector 7, interlocked multi-way valves 8 and 8', a vave 14 for switching the flow to the interlocked multi-way valve 8 or a by-pass line 17, n trapping columns 9 for trapping desired components, respectively, provided between the interlocked multi-way valves 8 and 8', and a recycle valve 18 provided downstream of the interlocked multiway valve 8'; an eluate collecting section comprising a common switch valve 20 for a washing solution 19 or another eluting solution 12, a pump 11 for supplying the washing solution 19 or another eluting solution 12, and fraction collectors 15 for collecting eluate fractions containing desired components from the trapping columns, respectively; and a controller 16 for controlling the respective control points, as shown in FIG. 4, based on the signals from the detector 7.

Figure 5:
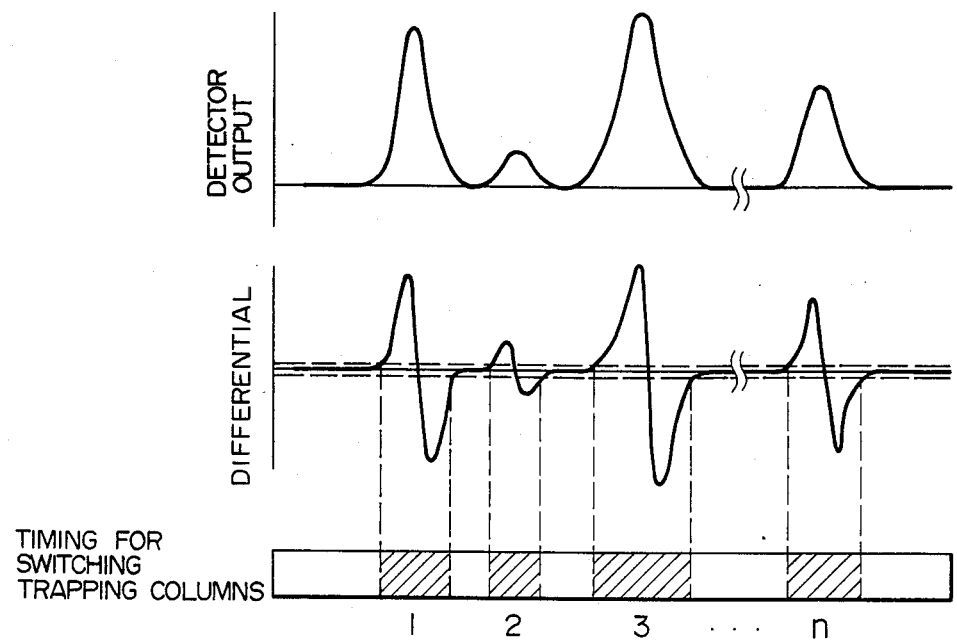
FIG. 5 is a correlation diagram among the detector output, differential with time, and trapping column switching schedule in the embodiment shown in FIG. 4.

A solution of a sample (raw material) containing proteins produced by propagation of *Escherichia coli* or cells obtained by genetic recombination technique is made into a sample solution 3 free from solid matters by extraction or by centrifuge, and the sample solution 3 is supplied to the separation column 6 by the pump 4 through the switch valve 5 to adsorb the desired components on the upper part in the separation column 6. After the supply of a predetermined amount of the sample solution, the pump 4 is stopped and the switch valve 5 is switched to supply the eluting solution 1 to the separation column 6 by starting the pump 2 according to the instructions from the controller 16. The adsorbed desired components such as albumin, interferon, etc. are developed and separated into the respective components. The resulting eluate from the separation column 6 is led to the detector 7, where a plurality of desired components are detected and plotted on a chromatogram as shown in FIG. 5. The rise and fall of the peaks are detected by way of differentials with time when they go beyond a predetermined range, as shown in FIG. 5, and the valve 14 and the interlocked multiway valves 8 and 8' are switched by the controller 16 to lead only the peak fractions containing the detected desired components to appropriate trapping columns 9, respectively. The eluate passing through the trapping columns 9 and the eluate by-passed through the by pass line 17 can be recycled again for reuse as the eluting solution or merely discarded to the outside by switching the valve 18.

Figure 7:
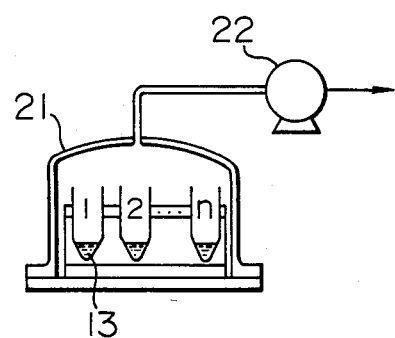
FIG. 7 is a schematic view of a drier for an ultimate eluate containing a desired component.
Figure 6:
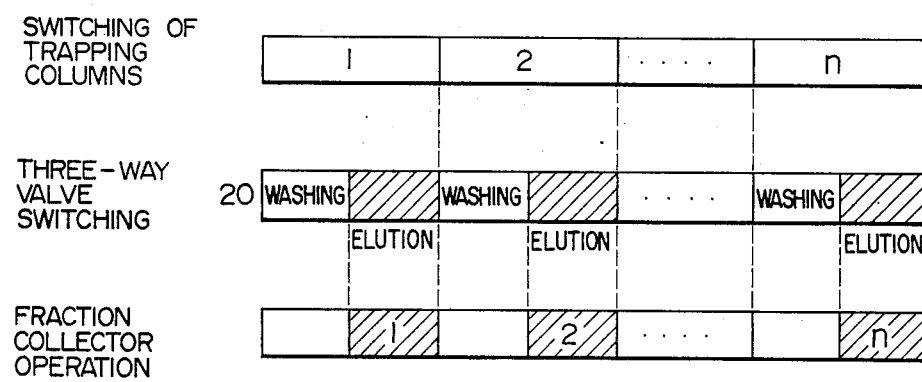
FIG. 6 is a correlation diagram of operating schedule in the embodiment shown in FIG. 4.

After the desired components have been trapped in the respective trapping columns 9, the pump 2 is stopped by the controller 16, and the valve 14 is switched and the pump 11 is driven to supply washing solution 19 to one of the trapping columns according to the sequence schedule shown as an example in FIG. 6. After the washing, the valve 20 is switched to supply another eluting solution 12 to the trapping column to elute the desired components trapped in the trapping columns, and the resulting eluates containing the desired components respectively from the trapping columns are collected into respective test tubes 13 or collecting bottles in a fraction collector 15. The thus obtained eluates containing the desired components, respectively, in the test tubes 13 or the collecting bottles are placed in a vacuum drier 21 schematically shown in FIG. 7 to remove other volatile matters than the desired components, thereby obtaining the desired components in pure forms. In FIG. 7, numeral 22 is a vacuum pump.

When a column for aqueous gel permeation chromatography (Gelpack W 530, trademark of a product made by Hitachi Kasei Kogyo K. K., Japan, 10.7 mm in inner diameter × 300 nm in length) was used as the separation column 6, anion exchange resin columns (CQP-30 DEAE, trademark of a product made by Mitsubishi Kasei Kogyo K. K., Japan, 6 mm in inner diameter×10 mm in length) as the trapping columns 9, an aqueous solution of 0.015M Na$_2$Co$_3$-0.015M NaHCO$_3$ as the eluting solution 1 for the separation column 6, and an aqueous 2M ammonium acetate solution as another eluting solution 12 for the trapping columns 9, protein components in serum as a sample solution could be fractionated and recovered in substantially 90–100% yield 4–5 hours after the charge of the sample solution to the separation column.

It was also found that it was possible in the fractionation and recovery of protein components in serum to use various combinations of adsorbents and eluting solutions, for example, ion exchange resin for the separation column 6, silica-octadecylsilane (Hitachi Gel No. 3063, trademark of a product made by Hitachi, Ltd., Japan) for the trapping columns 9 or hydrophobic chromatographic or distribution-adsorptive column filler of porous type (Hitachi Gel No. 3013, trademark of a product made by Hitachi, Ltd., Japan), an aqueous buffer solution as an eluting solution 1 for the separation column 6, and an aqueous solvent mixture containing a few tens percent of organic solvent such as acetonitrile as another eluting solution 12 for the trapping columns 9.

Various means usually used in the ordinary liquid chromatography such as 6-way switch valve, etc. can be also employed as the switch valve 5.

Figure 8:
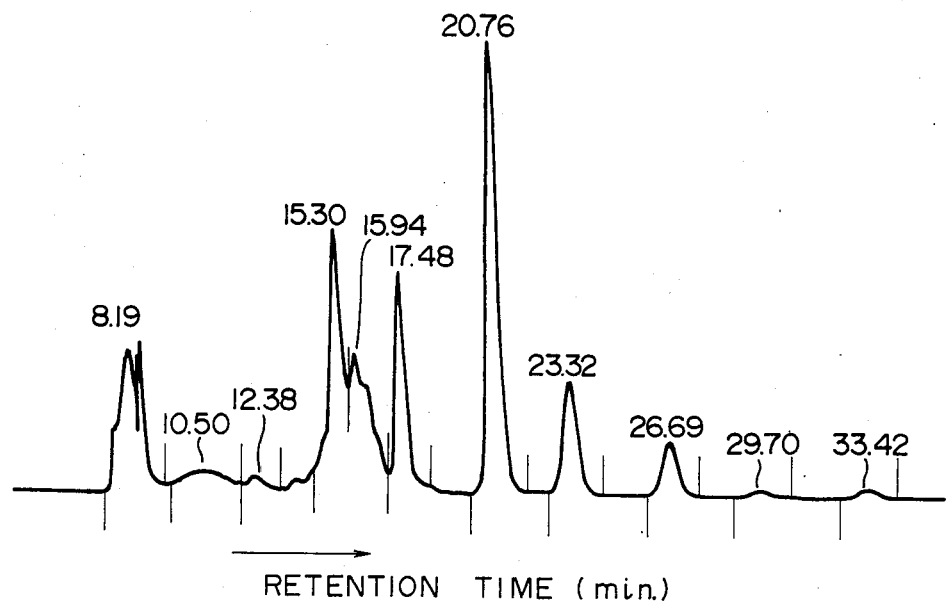
FIG. 8 is a chromatogram of crude extract product of β-galactosidase and FIG. 9 is a chromatogram of pure β-galactosidase separated and purified according to the embodiment shown in FIG. 4.
Figure 9:
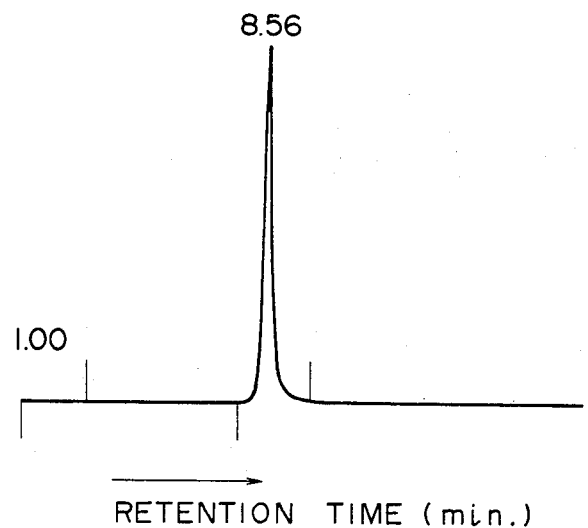

In the present invention, a most suitable buffer solution for the liquid chromatographic separatin can be used as an eluting solution 1 for the separation column 6, the eluate from the separation column 6 can be selectively passed through the respective trapping columns 9 according to the desired components to trap the desired components therein, while discarding or reusing the effluent eluate from the trapping columns 9, and the desired components trapped in the respective trapping columns 9 can be eluted with an aqueous solution of a volatile component when dried under reduced pressure, for example, ammonium acetate, ammonium carbonate, or organic solvents such as acetonitrile, etc. as an eluting solution for the trapping columns 9. The thus obtained second eluates containing the desired components from the trapping columns can be dried under reduced pressure, whereby the desired components can be obtained as the respective pure products. That is, in the present invention, separation and purification of components elutable as aqueous salt solutions such as protein components, polypeptide, DNA, etc. can be simply and economically carried out. For example, a crude extract β-galactosidase extract, whose chromatogram is shown in FIG. 8, could be fractionated and recovered into pure β-galactosidase product, whose chromatogram is shown in FIG. 9, according to the present liquid chromatography.

In the present invention, the fractionation and recovery can be carried out by trapping the desired components in small trapping columns without any accompanying eluting solution for the separation column 6, and thus the necessary space for storing the accompanying eluting solution can be saved, and also the desired components can be trapped as concentrated in the trapping column, or further can be accumulated in the repeated trapping operations, that is, by repeated charging in and elution from the separation column into the trapping columns As described above, the present invention can provide a liquid chromatography with simple isolation of desired components and an apparatus using the same, and thus has an industrially important significance.

What is claimed is:

1. A liquid chromatography process for isolating a desired component from a sample solution using a liquid state eluting solution, which comprises passing the sample solution through a separation column, thereby separating components contained therein in the separation column, then selectively eluting a desired component of the components separated in the separation olumn using an eluting solution capable of eluting the esired component from the separating column and nabling the desired component to be retained in a trapping column, passing the eluate containing the desired component from the separation column through a trapping column, thereby trapping the desired component in the trapping column, while discarding or recycling the effluent eluate from the trapping column, and then passing another elution solution composed of a volatile substance when dried under reduced pressure through the trapping column, thereby recovering eluate containing the desired component from the trapping column, wherein the recovered eluate from the trapping column is d under reduced pressure, thereby obtaining the desired component pure form.

2. A liquid chromatography process according to claim 1, wherein the eluate from the separation column is detected by a detector and an eluate fraction containing detected desirred component is introduced selectively into the trapping column.

3. A liquid chrom;atography process according to claim 2, wherein the eluate fraction from the separation column is selectively introduced into one of the trapping columns, and the detection and the introduction of the eluate containing the detected desired component into the trapping column are interlocked with each other.

4. A liquid chromatography process according to claim 2, wherein the eluate fraction from the separation column is selectively introduced into one of the trapping columns, t the introduction of the eluting solution into the apping column and the recovery of the resulting eluate om the trapping column are interlocked with each other.

5. A liquid chromatography process according to claim 1, wherein the eluting solution for the separation column is an aqueous solution or a buffer solution containing electrolytes. according to claim 1, 6. A liquid chromatography process wherein packing filled in the separation column is different from packing filled in the trapping column.

* * * * *